United States Patent
Dunham

(10) Patent No.: US 7,085,352 B2
(45) Date of Patent: Aug. 1, 2006

(54) ELECTRON EMITTER ASSEMBLY AND METHOD FOR GENERATING ELECTRON BEAMS

(75) Inventor: Bruce Matthew Dunham, Mequon, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 10/710,275

(22) Filed: Jun. 30, 2004

(65) Prior Publication Data

US 2006/0002514 A1   Jan. 5, 2006

(51) Int. Cl.
*H01J 35/00* (2006.01)
(52) U.S. Cl. .................... 378/122; 378/9; 313/373; 313/380
(58) Field of Classification Search .............. 378/4–20, 378/119, 122; 313/373, 375, 376, 380, 383, 313/542, 544
See application file for complete search history.

(56) References Cited

U.S. PATENT DOCUMENTS

| | | | |
|---|---|---|---|
| 4,198,675 A | 4/1980 | Moore | 372/26 |
| 4,236,080 A * | 11/1980 | Heinzerling | 378/19 |
| 4,606,061 A | 8/1986 | Ramamurti | 378/119 |
| 5,042,058 A | 8/1991 | Rentzepis | 378/122 |
| 5,485,371 A * | 1/1996 | Ito et al. | 378/20 |
| 5,680,431 A | 10/1997 | Pietras, III et al. | 378/119 |
| 6,181,765 B1 | 1/2001 | Sribar et al. | 378/10 |
| 6,272,199 B1 | 8/2001 | Sembritzki et al. | 378/14 |
| 6,385,292 B1 * | 5/2002 | Dunham et al. | 378/122 |
| 6,516,048 B1 | 2/2003 | Mori | 378/119 |

OTHER PUBLICATIONS

Pending U.S. Appl. No. 10/904,254, filed Nov. 2, 2004.
Pending U.S. Appl. No. 10/904,280, filed Nov. 2, 2004.
Pending U.S. Appl. No. 10/904,286, filed Nov. 2, 2004.

* cited by examiner

*Primary Examiner*—Edward J. Glick
*Assistant Examiner*—Jurie Yun
(74) *Attorney, Agent, or Firm*—Cantor Colburn LLP

(57) ABSTRACT

An electron emitter assembly and a method for generating electron beams are provided. The electron emitter assembly includes a light source configured to emit light. The electron emitter assembly further includes a photo-responsive device operably coupled to an electron emitter device. The photo-responsive device induces the electron emitter device to emit electrons in response to receiving the light. Finally, the electron emitter assembly includes an anode receiving the emitted electrons from the electron emitter device.

27 Claims, 7 Drawing Sheets

ELECTRON EMITTER ASSEMBLY AND METHOD FOR GENERATING ELECTRON BEAMS

BACKGROUND OF INVENTION

X-ray devices have utilized electron emitter devices, such as field emitter arrays, to generate x-rays. Each field emitter array is coupled to an electrical control line that extends through the vacuum enclosure wherein a voltage signal applied over the control line induces the field emitter array to emit electrons. The emitted electrons are thereafter utilized to generate x-rays. Accordingly, because the x-ray device can utilize thousands of field emitter arrays having thousands of electrical control lines, a problem exists in routing the electrical control lines through apertures in a wall of the vacuum enclosure and providing a vacuum seal around each control line.

Thus, there is a need for an electron emitter assembly that eliminates the need for routing electrical control lines through a wall of a vacuum enclosure to provide signals for inducing electron emitter assembly to emit electrons.

BRIEF DESCRIPTION OF THE INVENTION

An electron emitter assembly in accordance with an exemplary embodiment is provided. The electron emitter assembly includes a light source configured to emit light. The electron emitter assembly further includes a photo-responsive device operably coupled to an electron emitter device. The photo-responsive device induces the electron emitter device to emit electrons in response to receiving the light. Finally, the electron emitter assembly includes an anode receiving the emitted electrons from the electron emitter device.

An electron emitter assembly in accordance with another exemplary embodiment is provided. The electron emitter assembly includes a light source configured to emit light. The electron emitter assembly further includes a plurality of photo-responsive devices and a plurality of electron emitter devices. Each photo-responsive device is operably coupled to a corresponding electron emitter device. Each photo-responsive device induces the corresponding electron emitter device to emit electrons in response to the photo-responsive device receiving at least a portion of the light. Finally, the electron emitter assembly includes an anode receiving the emitted electrons from each of the electron emitter devices.

An electron emitter assembly in accordance with another exemplary embodiment is provided. The electron emitter assembly includes a first light source configured to emit light having a first wavelength. The electron emitter assembly further includes a second light source configured to emit light having a second wavelength. The electron emitter assembly further includes first and second photo-responsive devices operably coupled to an electron emitter device. The electron emitter device includes a first electron emitter subassembly and a second electron emitter subassembly. The first photo-responsive device induces the first electron emitter subassembly to emit electrons in response to receiving the light having the first wavelength. The second photo-responsive device induces the second electron emitter subassembly to emit electrons in response to receiving the light having the second wavelength. Finally, the electron emitter assembly includes an anode receiving the emitted electrons from the electron emitter device.

A method for generating an electron beam in accordance with another exemplary embodiment is provided. The method includes emitting light onto a photo-responsive device operably coupled to an electron emitter device. The method further includes energizing the electron emitter device to emit electrons towards an anode in response to the photo-responsive device receiving the light.

A method for generating electron beams in accordance with another exemplary embodiment is provided. The method includes emitting light having a first wavelength onto a first photo-responsive device operably coupled to an electron emitter device. The electron emitter device has a first electron emitter subassembly and a second electron emitter subassembly. The method further includes energizing the first electron emitter subassembly to emit electrons towards an anode in response to the first photo-responsive device receiving the light having the first wavelength. The method further includes emitting light having a second wavelength onto a second photo-responsive device operably coupled to the electron emitter device. Finally, the method includes energizing the second electron emitter subassembly to emit electrons towards the anode in response to the second photo-responsive device receiving the light having the second wavelength.

DETAILED DESCRIPTION

Figure 1:
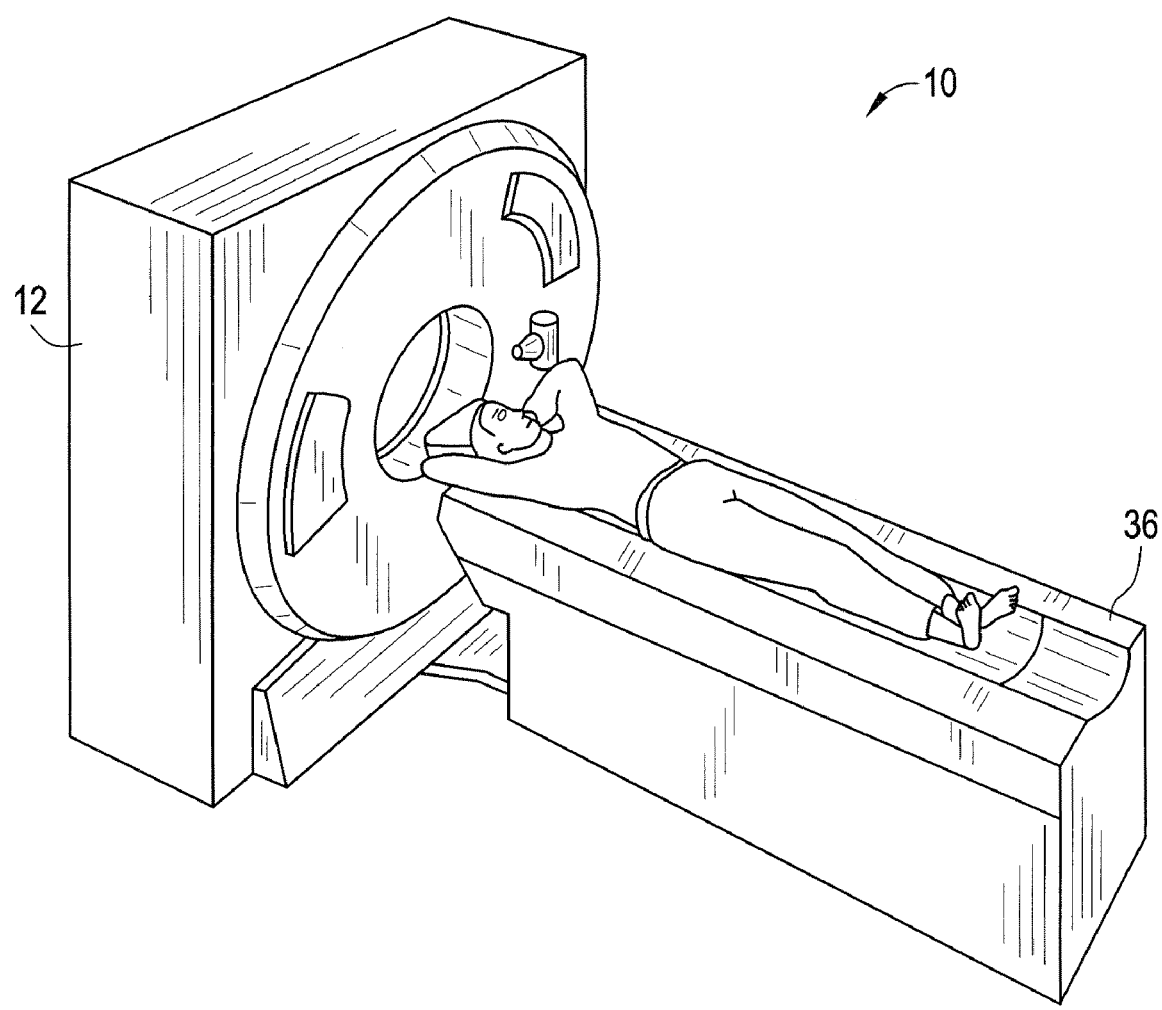
FIG. 1 is a schematic of a CT imaging system in accordance with exemplary embodiment.
Figure 2:
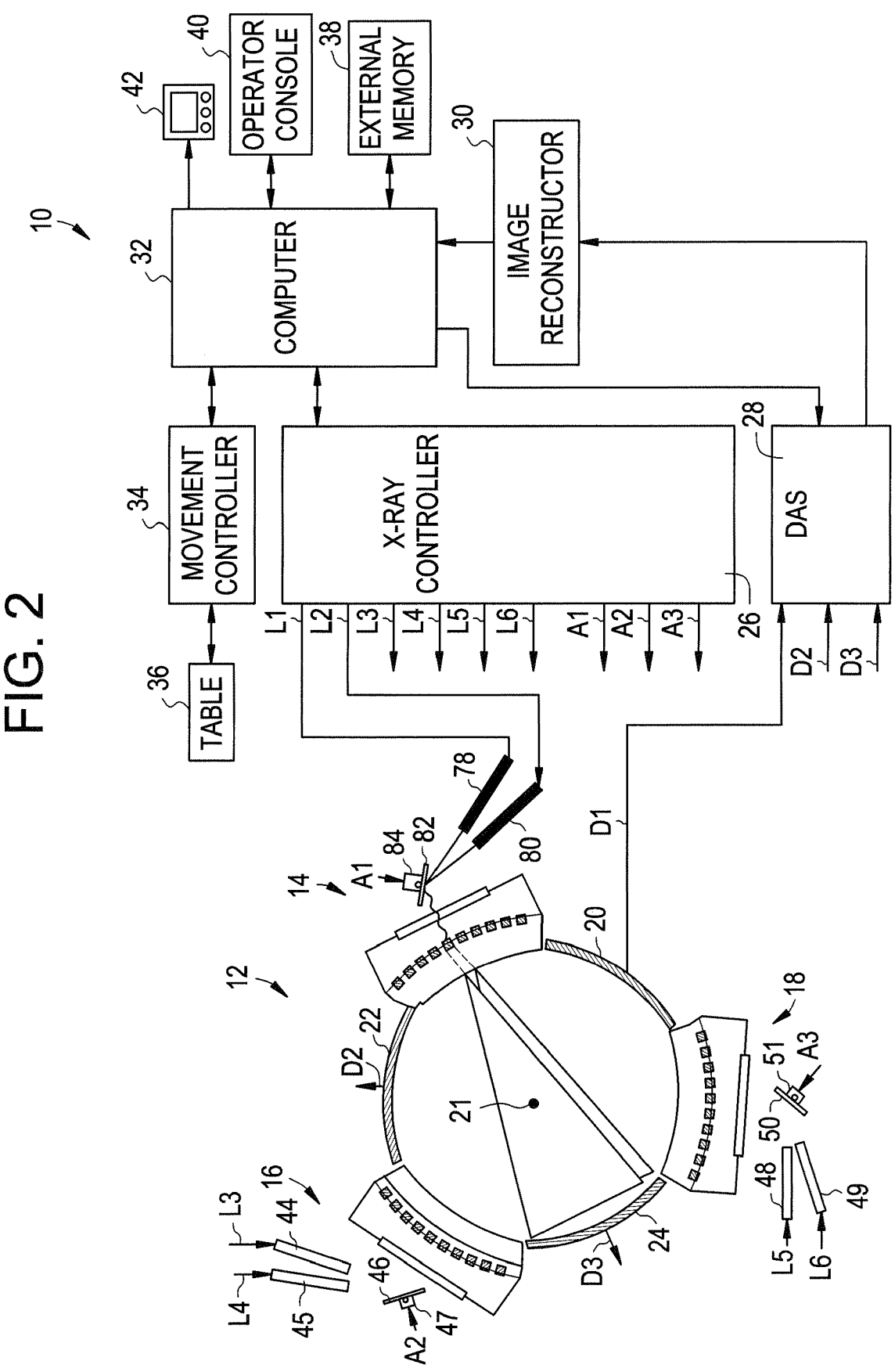
FIG. 2 is a more detailed schematic of the CT imaging system of FIG. 1.

Referring to FIGS. 1 and 2, a CT imaging system 10 for generating digital images of a target object in accordance with an exemplary embodiment is shown. The CT imaging system 10 includes a CT scanner 12 including x-ray source subassemblies 14, 16, 18 and x-ray detector arrays 20, 22, 24, an x-ray controller 26, a data acquisition system 28, an image reconstructor 30, a computer 32, a movement controller 34, a table 36, an external memory 38, an operator console 40, and a computer monitor 42. It should be noted that in an alternate embodiment, CT imaging system 10 can have more than or less than three x-ray source subassemblies. Further, CT imaging system 10 can have more than or less than three x-ray detector arrays.

The CT scanner 12 is provided to generate a plurality of digital images of a target object. The CT scanner 12 includes the x-ray source subassemblies 14, 16, 18 and the x-ray detector arrays 20, 22, 24. Each x-ray source subassembly includes an x-ray detector array disposed directly across a scanning region from the x-ray source subassembly to receive attenuated x-rays passing through a target object. For example, the x-ray source subassembly 14 has the x-ray detector array 24 disposed directly across from the subassembly 14 to receive x-rays passing through a target object 21 disposed therebetween. Similarly, the x-ray source subassembly 16 has the x-ray detector array 20 disposed directly across from the subassembly 16 to receive x-rays passing through the target object 21 disposed therebetween. Similarly, the x-ray source subassembly 18 has the x-ray detector array 22 disposed directly across from the subassembly 18 to receive x-rays passing through the target object 21 disposed therebetween. Further, each x-ray source subassembly is disposed between two adjacent x-ray detector arrays. For example, the x-ray source subassembly 14 is disposed between the x-ray detector arrays 22 and 20. Similarly, the x-ray source subassembly 16 is disposed between the x-ray detector arrays 22 and 24. Similarly, the x-ray source subassembly 18 is disposed between the x-ray detector arrays 24 and 20. Because each of the subassemblies 14, 16, 18 have a substantially identical structure, only subassembly 14 will be described in detail for purposes of simplicity.

Figure 3:
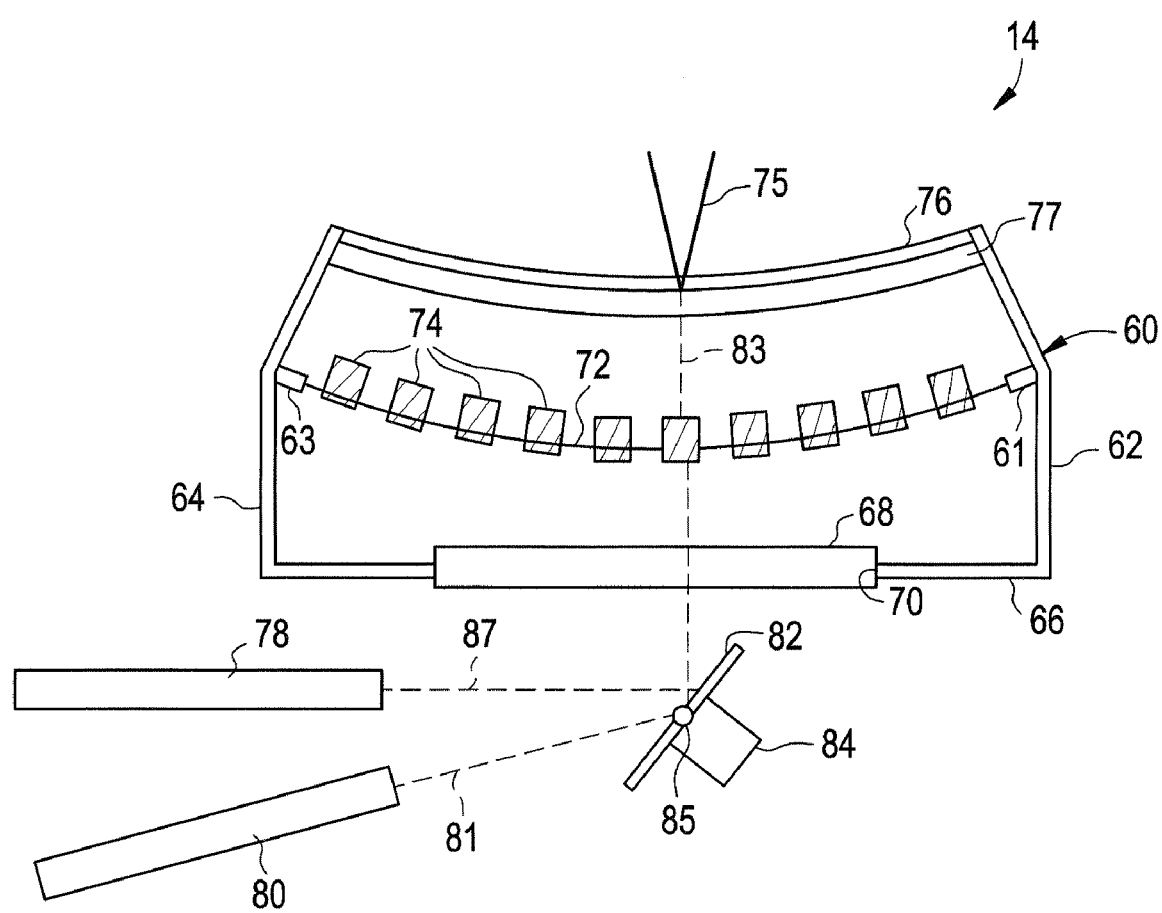
FIG. 3 is a schematic of an x-ray source subassembly utilized in the CT imaging system of FIG. 1.

Referring to FIG. 3, the x-ray source subassembly 14 is provided to generate an x-ray beam 75 in response to receiving a light from a laser. The subassembly 14 includes a vacuum housing 60, a window 68, a substrate 72, insulating supports 61, 63, a plurality of electron emitter assemblies 74, an x-ray transmissive window 76, an anode 77, lasers 78, 80, a mirror 82, and an actuator 84. The vacuum housing 60 includes sidewalls 62, 64 coupled to a bottom wall 66. The bottom wall 66 defines an aperture 70 for receiving the window 68 therein. The insulating supports 61, 63 are coupled to sidewalls 62, 64, respectively. The insulating supports 61, 63 electrically isolate the substrate 72 from the housing 60 and holds the substrate 72 therebetween. The substrate 72 is provided to hold the plurality of electron emitter assemblies 74 thereon. Each of the electron emitter assemblies 74 is disposed through a corresponding aperture in the substrate 72 and is fixedly held in the aperture. Each of the electron emitter subassemblies 74 are electrically coupled to a voltage source 110 via an electrical lines 88, 113 that extend through one of the sidewalls 62, 64. The sidewalls 62 and 64 define an opening opposite the bottom wall 66 for receiving the anode film 77 and the x-ray transmissive window 76 disposed adjacent the anode film 77. The vacuum housing 60 is constructed from stainless steel and is vacuum-sealed to maintain a vacuum therein.

The mirror 82 is provided to reflect light from one or more of the lasers 78, 80 through the window 68 onto one or more of the electron emitter assemblies 74. In response to receiving one or more of the light beams 81, 87, each electron emitter assembly 74 is configured to generate an electron beam 83 that is received by the anode 77. In response to receiving the emitted electrons, the anode 77 generates an x-ray beam 75 that propagates through the x-ray transmissive window 76. The mirror 82 is rotated at a pivot point 85 by the motion actuator 84 about at least two axes. In particular, the mirror 82 can be rotated at the pivot point 85 at least 120° about each of two axes such that light from each of the lasers 78, 80 can be selectively directed towards each of the plurality of electron emitter assemblies 74. In an alternative embodiment, a second mirror could be utilized in the x-ray source subassembly 14 wherein mirror 82 could reflect light from laser 78 and the second mirror could reflect light laser 80.

The lasers 78, 80 are provided to generate light beams 87, 81, respectively, for inducing the plurality of electron emitter assemblies 74 to emit electrons, for subsequently generating x-rays. The laser 80 emits a light having a first predetermined wavelength and the laser 78 emits a light having a second predetermined wavelength different from the first predetermined wavelength.

Figure 4:
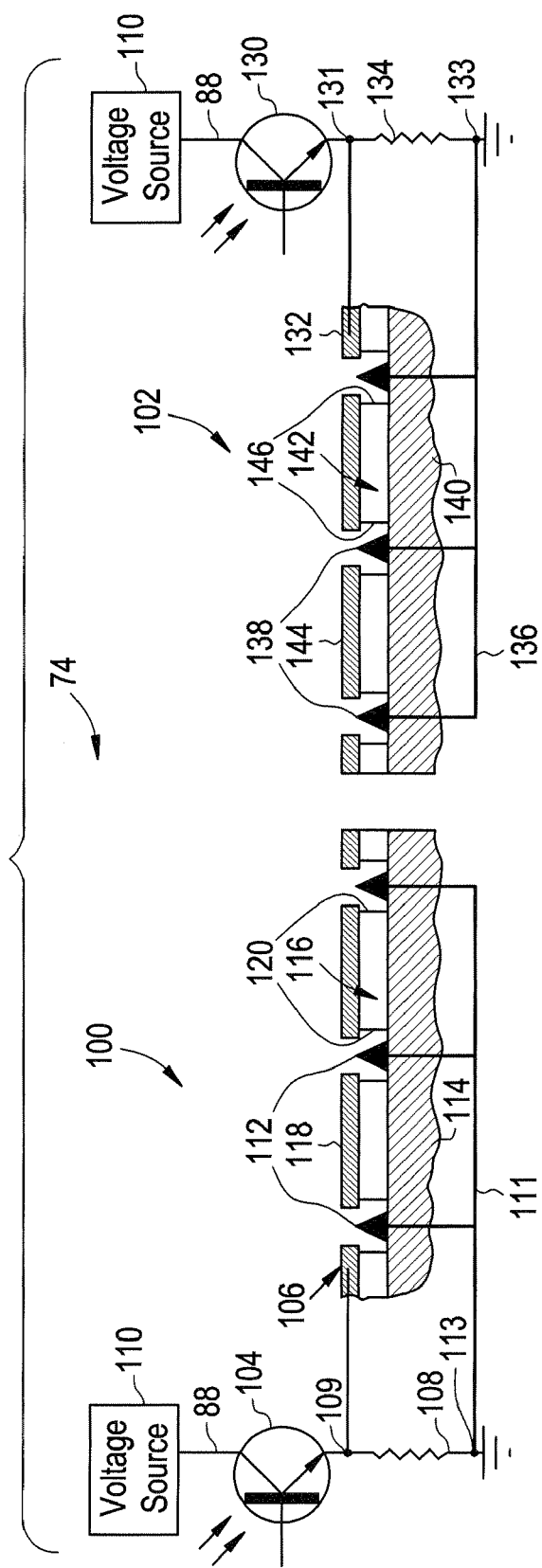
FIG. 4 is a circuit schematic of an electron emitter assembly utilized in the x-ray source subassembly of FIG. 3 in accordance with an exemplary embodiment.
Figure 5:
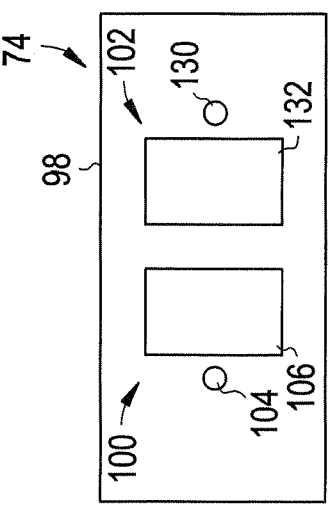
FIG. 5 is a top view of the electron emitter assembly of FIG. 4 in accordance with an exemplary embodiment.

Referring to FIGS. 4 and 5, each electron emitter assembly 74 includes a vacuum housing 98, an electron emitter subassembly 100, and an electron emitter subassembly 102. The electron emitter subassembly 100 is provided to emit first and second electron beams responsive to first and second light beams, respectively, from lasers 80, 78 having first and second wavelengths, respectively.

The electron emitter subassembly 100 includes a photo-transistor 104, a electron emitter device (e.g., field emitter array) 106, a resistor 108, a voltage source 110, and an electrical line 111. The photo-transistor 104 is operably coupled at a node 109 to both a resistor 108 and the field emitter array 106. The field emitter array 106 is connected in parallel with the resistor 108 between the node 109 and a node 113, the node 113 further coupled to a voltage ground. When the photo-transistor 104 receives light having a first wavelength from the laser 80, the transistor 104 applies voltage from a voltage source 110 to the field emitter array 106 that induces the array 106 to emit electrons.

The field emitter array 106 includes a plurality of metal tips 112, a silicon base 114, a dielectric layer 116, and a metal layer 118. The dielectric layer 116 is operably coupled to the silicon base 114. The base 114 can be constructed from materials other than silicon including for example other semiconductor materials. The metal layer 118 is operably coupled to the dielectric layer 116 opposite the silicon base 114. The combination of the metal layer 118 and the dielectric layer 116 include a plurality of apertures 120 disposed therethrough. Each aperture 120 has a diameter larger than a corresponding metal tip 112 such that the corresponding metal tip 112 is disposed within the aperture 120. Further, each metal tip 112 is operably coupled to the silicon base 114. Each metal tip 112 is electrically connected to the node 113 via an electrical line 111. Further, the metal layer 118 is electrically connected to the node 109 for receiving a voltage from the photo-transistor 104. In response to the photo-transistor 104 applying a voltage between the metal layer 118 and the metal tips 112, each of the metal tips 112 emits electrons toward the anode 77. It should be further noted that a high voltage source (not shown) is operably coupled between each of the plurality of electron emitter assemblies 74 and the anode 77 to apply a high voltage therebetween to accelerate electrons being emitted from the assemblies 74 toward the anode 77. In alternate embodiments, the plurality of metal tips 112 can be replaced with nanorods, carbon nanotubes, or equivalent structures configured to emit electrons.

The electron emitter subassembly 102 includes a photo-transistor 130, a field emitter array 132, a resistor 134, the voltage source 110, and an electrical line 136. The photo-transistor 130 is operably coupled at a node 131 to both a resistor 134 and the field emitter array 132. The field emitter array 132 is connected in parallel with the resistor 134 between the node 131 and a node 133, the node 133 is further coupled to a voltage ground. When the photo-transistor 130 receives light having a second wavelength from the laser 78, the photo-transistor 130 applies a voltage from the voltage source 110 to the field emitter array 132 that induces the array 132 to emit electrons.

The field emitter array 132 includes a plurality of metal tips 138, a silicon base 140, a dielectric layer 142, and a metal layer 144. The dielectric layer 142 is operably coupled to the silicon base 140. The metal layer 144 is operably coupled to the dielectric layer 142 opposite the silicon base 140. The combination of the metal layer 144 and the dielectric layer 142 include a plurality of apertures 146 disposed therethrough. Each aperture 146 has a diameter larger than a corresponding metal tip 138 such that the corresponding metal tip 138 is disposed within the aperture 146. Further, each metal tip 138 is operably coupled to the silicon base 140. Each metal tip 138 is electrically connected to the node 133 via an electrical line 136. Further, the metal layer 144 is electrically connected to the node 131 for receiving a voltage from the photo-transistor 130. In response to the photo-transistor 130 applying a voltage between the metal layer 132 and the metal tips 138, each of the metal tips 138 emit electrons toward the anode 77.

Referring to FIG. 5, the photo-transistor 104 is disposed adjacent the field emitter array 106 having a generally rectangular periphery. Similarly, the photo-transistor 130 is disposed adjacent the field emitter array 132 having a generally rectangular periphery. When the laser 80 emits a light having a first wavelength that is reflected by the mirror 82 onto the phototransistor 104, the field emitter array 106 emits electrons toward the anode 77, which are subsequently used to generate x-rays. Similarly, when the laser 78 emits a light having a second wavelength that is reflected onto the phototransistor 130, the field emitter array 132 emits electrons toward the anode 77, which are subsequently used to generate x-rays. Thus, by emitting light at the first wavelength toward the photo-transistor 104, and then subsequently emitting light at the second wavelength toward the photo-transistor 130, the anode 77 generates a first x-ray beam at a first focal point and a second x-ray beam at a second focal point that are utilized to generate to digital images of the target object 21.

Figure 6:
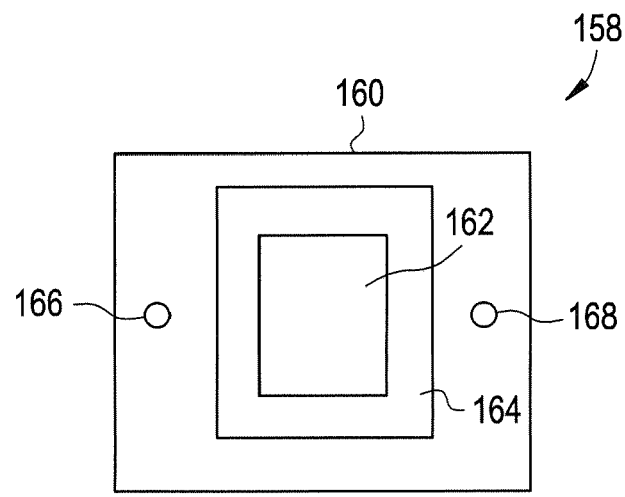
FIG. 6 is a top view of the electron emitter assembly in accordance with another exemplary embodiment.

Referring to FIG. 6, an alternate embodiment of an electron emitter assembly that can be utilized in the subassemblies 14, 16, 18 is illustrated. In particular, the electron emitter assembly 158 includes a vacuum housing 160, a first electron emitter assembly having a field emitter array 162, a second electron emitter assembly having a field emitter array 164, and photo-transistors 166, 168. The field emitter array 162 has a generally rectangular periphery and is surrounded by the field emitter array 164 also having a generally rectangular periphery. The photo-transistor 166 is operably coupled to the field emitter array 162 and is disposed adjacent a first edge of the vacuum housing 160. The phototransistor 168 is operably coupled to the field emitter array 164 and is disposed adjacent a second edge of the vacuum housing 160. When the laser 80 emits a light having a first wavelength that is reflected by the mirror 82 onto the phototransistor 166, the field emitter array 162 emits electrons toward the anode 77 having a relatively small diameter for obtaining a relatively small diameter x-ray beam (e.g., x-ray beam having a diameter of 200 microns). Additionally, when the laser 78 simultaneously emits a light having a second wavelength that is reflected onto the phototransistor 168, the field emitter array 164 emits electrons toward the anode 77 having a relatively large diameter for obtaining a relatively large diameter x-ray beam (e.g., x-ray beam having a diameter greater than 200 microns). Thus, by emitting light at the first wavelength toward the photo-transistor 166, and then subsequently emitting light at both the first and second wavelengths toward the photo-transistors 166, 168, the anode 77 generates a first x-ray beam having a first focal point diameter and a second x-ray beam having a second focal point diameter that are utilized to generate digital images of the target object 21.

Figure 7:
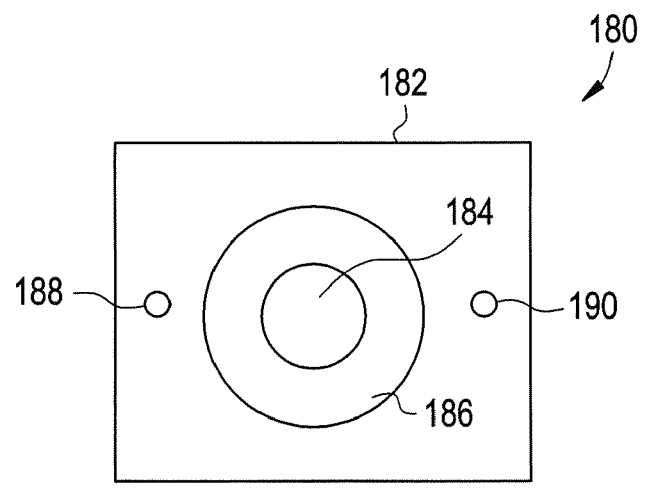
FIG. 7 is a top view of the electron emitter assembly in accordance with another exemplary embodiment.

Referring to FIG. 7, an alternate embodiment of an electron emitter assembly that can be utilized in the assemblies 14, 16, 18 is illustrated. In particular, the electron emitter assembly 180 includes a vacuum housing 182, a first electron emitter assembly having a field emitter array 184, a second electron emitter assembly having a field emitter array 186, and phototransistors 188, 190. The field emitter array 184 has a generally circular periphery and is surrounded by the field emitter array 186 having a generally circular periphery. The photo-transistor 188 is operably coupled to the field emitter array 184 and is disposed adjacent a first edge of the vacuum housing 182. The photo-transistor 190 is operably coupled to the field emitter array 186 and is disposed adjacent a second edge of the vacuum housing 182. When the laser 80 emits a light having the first wavelength that is reflected by the mirror 82 onto the phototransistor 188, the field emitter array 184 emits electrons toward the anode 77, having a relatively small diameter for obtaining a relatively small diameter x-ray beam (e.g., x-ray beam having a diameter of 200 microns). Additionally, when the laser 78 simultaneously emits a light having the second wavelength that is reflected onto the phototransistor 190, the field emitter array 186 emits electrons toward the anode 77, having a relatively large diameter for obtaining a relatively large diameter x-ray beam (e.g., x-ray beam having a diameter greater than 200 microns). Thus, by emitting light at the first wavelength toward the photo-transistor 188, and then subsequently emitting light at both the first and second wavelengths toward the phototransistors 188, 190, the anode 77 generates a first x-ray beam having a first focal point diameter and a second x-ray beam having a second focal point diameter that are utilized to generate digital images of the target object 21.

Figure 8:
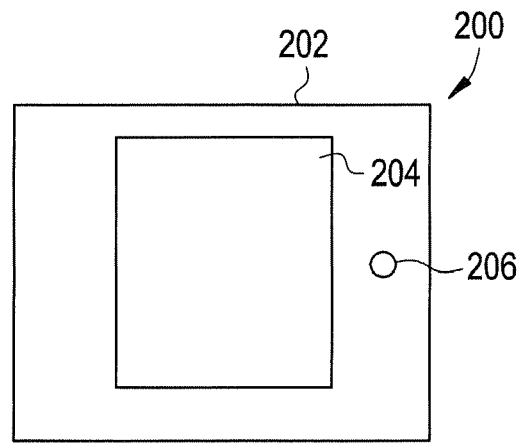
FIG. 8 is a top view of the electron emitter assembly in accordance with another exemplary embodiment.
Figure 9:
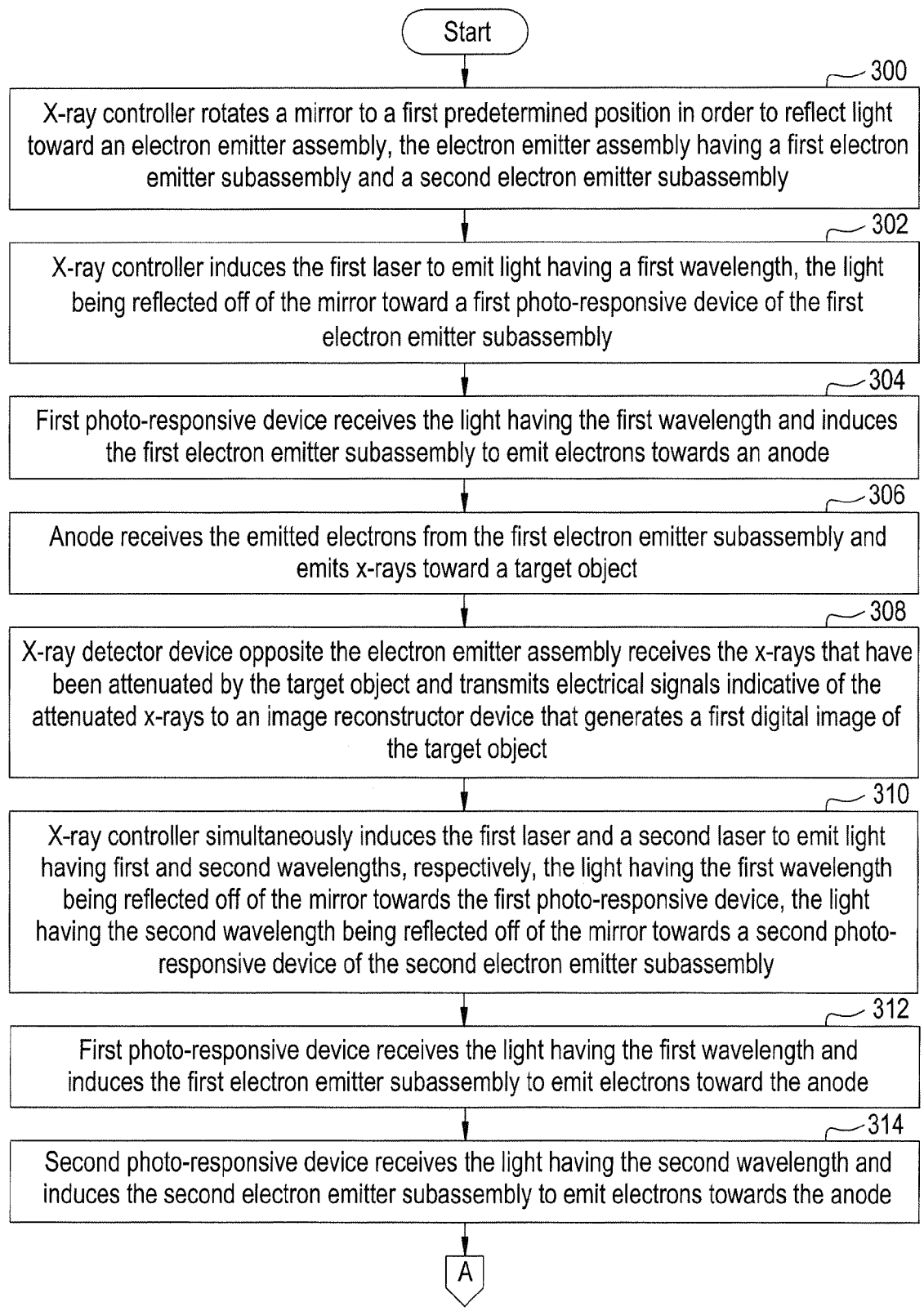
FIGS. 9–10 are flowcharts of the method for generating x-rays utilizing a method for generating electron beams in accordance with an exemplary embodiment.
Figure 10:
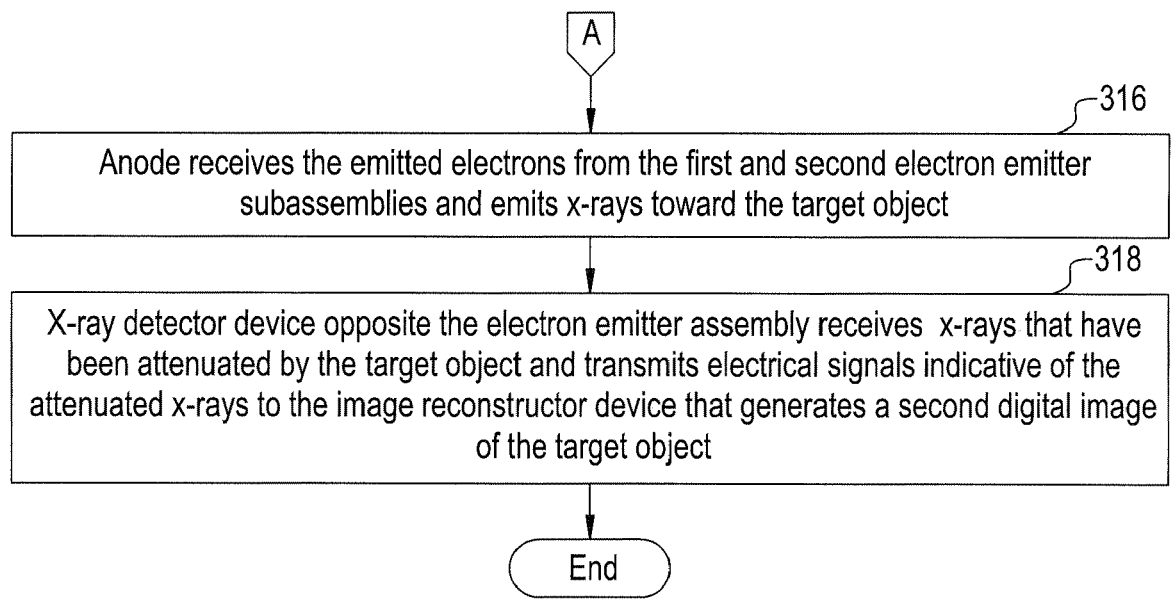

Referring to FIG. 8, an alternate embodiment of an electron emitter assembly that can be utilized in the assemblies 14, 16, 18 is illustrated. In particular, the electron emitter assembly 200 includes a vacuum housing 202, an electron emitter subassembly having a field emitter array 204, and a photo-transistor 206. The field emitter array 204 has a generally rectangular periphery. It should be noted, however, the emitter array 204 could have any known shape, including for example a circular shape, a triangular shape, a hexagonal shape, and an oval shape. When the laser 80 emits a light having the first wavelength that is reflected by the mirror 82 onto the photo-transistor 206, the field emitter array 204 emits electrons toward the anode 77, which are subsequently used to generate x-rays. Thus, because the photo-transistor 206 is activated in response to light having the first wavelength, only one laser would be needed to induce the field emitter array 204 to emit electrons. Thus, a plurality of electron emitter assemblies 200 could be activated utilizing one laser.

It should be noted, that in any of the embodiments of the electron emitter assemblies, that photo-transistors could be replaced with other photo-responsive devices, such as photo-diodes for example.

Referring to FIG. 2, the x-ray controller 26 is provided to control the CT scanner 12 in response to a control signal received from the computer 32. The x-ray controller 26 is operably coupled to the lasers 78, 80, 44, 45, 48, 49, the motion actuators 84, 47, 51, and the computer 32. Further, the x-ray controller 26 generates control signals L1, L2, L3, L4, L5, L6 to induce lasers 78, 80, 44, 45, 48, 49, respectively, to emit light which results in x-ray beams being generated. Further, the x-ray controller 26 generates control signals A1, A2, A3 to control movement of the mirrors 82, 46, 50 by actuators 84, 47, 51, respectively.

The data acquisition system 28 is operably coupled to the x-ray detector arrays 20, 22, 24 and is further operably coupled to the computer 32 and to image reconstructor 30. The system 28 receives signals D1, D2, D3 from the x-ray detector arrays 20, 22, 24, respectively and transfers the signals to the image reconstructor 30.

The image reconstructor 30 is provided to generate digital images from the signals D1, D2, D3. The image reconstructor 30 is operably coupled between the data acquisition system 28 and the computer 32. The image reconstructor 30 transmits the generated digital images to the computer 32.

The computer is operably coupled to the x-ray controller 26, the data acquisition system 28, the image reconstructor 30, the external memory 38, a computer console 40, a computer monitor 42, and the movement controller 34.

The computer 32 is provided to generate a first control signal that induces the movement controller 34 to move the table 36 to a predetermined position. Further, the computer 32 generates a second control signal that induces the x-ray controller 26 to initiate generating x-ray beams. Further, the computer 32 receives the generated digital images from the image reconstructor 30 and either displays the images on the monitor 42 or stores the digital images in the external memory 38, or both. The operator console 40 is operably coupled to the computer 32 to allow user to request specific digital images to view.

Referring to FIGS. 2, 3, 4, 9, and 10, a method for generating x-rays in accordance with an exemplary embodiment will now be explained. For purposes of discussion, the method will be explained utilizing the x-ray source subassembly 14 having the electron emitter assembly 74. It should be noted, however, that in alternate embodiments the electron emitter assemblies 158, 180, 200 could be utilized instead of the electron emitter assembly 74. Further, the method will be explained utilizing only one electron emitter assembly 74 emitting two x-ray beams. However it will be understood that the method would be iteratively performed for each electron emitter assembly 74 in the x-ray source subassemblies 14, 16, 18 to generate a plurality of x-ray beams.

At step 300, the x-ray controller 26 rotates the mirror 82 to a first predetermined position in order to reflect light toward the electron emitter assembly 74, the electron emitter assembly 74 having the electron emitter subassembly 100 and the electron emitter subassembly 102.

At step 302, the x-ray controller 26 induces the laser 80 to emit light having a first wavelength, the light being reflected off of the mirror 82 toward the photo-transistor 104.

At step 304, the photo-transistor 104 receives the light having the first wavelength and induces the electron emitter subassembly 100 to emit electrons towards the anode 77.

At step 306, the anode 77 receives the emitted electrons from the electron emitter subassembly 100 and emits x-rays toward a target object.

At step 308, the x-ray detector array 24 opposite the electron emitter assembly 74 receives the x-rays that have been attenuated by the target object and transmits electrical signals indicative of the attenuated x-rays to an image reconstructor device 30 that generates a first digital image of the target object.

At step 310, the x-ray controller 26 simultaneously induces the lasers 78, 80 to emit light having first and second wavelengths, respectively. The light having the first wavelength is reflected off of the mirror 82 towards the first photo-transistor 104. The light having the second wavelength is reflected off of the mirror 82 towards the second photo-transistor 130.

At step 312, the photo-transistor 104 receives the light having the first wavelength and induces the electron emitter subassembly 100 to emit electrons towards the anode 77.

At step 314, the photo-transistor 130 receives the light having the second wavelength and induces the electron emitter subassembly 102 to emit electrons towards the anode 77.

At step 316, the anode 77 receives the emitted electrons from the electron emitter subassemblies 100, 102 and emits x-rays toward the target object.

At step 318, the x-ray detector array 24 opposite the electron emitter assembly 102 receives the x-rays that have been attenuated by the target object and transmits electrical signals indicative of the attenuated x-rays to the image reconstructor device 30 that generates a second digital image of the target object.

The system and method for generating x-rays provides a substantial advantage over other systems and methods. In particular, the system provides technical effect of utilizing light beams to actuate electron emitter assemblies in x-ray source subassemblies to generate electron beams that are used to subsequently generate x-rays. Thus, the system does not require a plurality of control lines to be routed through a wall of a vacuum housing to the electron emitter assemblies, as done in other systems, which can result in vacuum sealing problems and associated vacuum leaks within the vacuum housing.

While embodiments of the invention are described with reference to the exemplary embodiments, it will be understood by those skilled in the art that various changes may be made and equivalence may be substituted for elements thereof without departing from the scope of the invention. In addition, many modifications may be made to the teachings of the invention to adapt to a particular situation without departing from the scope thereof. Therefore, it is intended that the invention not be limited to the embodiment disclosed for carrying out this invention, but that the invention includes all embodiments falling with the scope of the intended claims. Moreover, the use of the term's first, second, etc. does not denote any order of importance, but rather the term's first, second, etc. are used to distinguish one element from another. Furthermore, the use of the terms a, an, etc. do not denote a limitation of quantity, but rather denote the presence of at least one of the referenced items.

What is claimed is:

1. An electron emitter assembly, comprising:
   a light source configured to emit light;
   a housing having a light receiving window configured to allow light from the light source to pass therethrough;
   a photo-responsive device disposed in the housing configured to receive the light passing through the light receiving window, the photo-responsive device operably coupled to an electron emitter device, the photo-responsive device applying a voltage to the electron emitter device in response to receiving the light to induce the electron emitter device to emit electrons; and
   an anode disposed in the housing, the anode receiving the emitted electrons from the electron emitter device.

2. The electron emitter assembly of claim 1, wherein the anode is configured to emit x-rays in response to receiving the emitted electrons from the electron emitter device.

3. The electron emitter assembly of claim 2, wherein
the housing further comprises an x-ray transmissive window being disposed in an aperture extending through a wall of the housing, wherein the anode emits x-rays through the x-ray transmissive window in response to receiving the emitted electrons from the electron emitter device.

4. The electron emitter assembly of claim 1, wherein the electron emitter device comprises a field emitter array.

5. The electron emitter assembly of claim 1, wherein the light source comprises a laser.

6. The electron emitter assembly of claim 1, further comprising a mirror configured to receive light from the light source and to reflect the light towards the photo-responsive device.

7. The electron emitter assembly of claim 6, wherein the mirror can rotate about at least two axes.

8. The electron emitter assembly of claim 1, wherein the photo-responsive device comprises one of a photodiode and a photo-transistor.

9. An electron emitter assembly, comprising:
a light source configured to emit light;
a housing having a light receiving window configured to allow light from the light source to pass therethrough;
a plurality of photo-responsive devices disposed in the housing configured to receive the light passing through the light receiving window and a plurality of electron emitter devices disposed in the housing, each photo-responsive device being operably coupled to a corresponding electron emitter device, each photo-responsive device applying a voltage to the electron emitter device to induce the corresponding electron emitter device to emit electrons in response to the photo-responsive device receiving at least a portion of the light; and
an anode disposed in the housing receiving the emitted electrons from each of the electron emitter devices.

10. The electron emitter assembly of claim 9, wherein the anode is configured to emit x-rays in response to receiving the emitted electrons from the electron emitter device.

11. The electron emitter assembly of claim 10, wherein
the housing further comprises an x-ray transmissive window being disposed in an aperture extending through a wall of the housing, wherein the anode emits x-rays through the x-ray transmissive window in response to receiving the emitted electrons from the electron emitter device.

12. The electron emitter assembly of claim 9, wherein each electron emitter device comprises a field emitter array.

13. The electron emitter assembly of claim 9, further comprising a mirror configured to receive light from the light source and to reflect the light towards at least one of the photo-responsive devices.

14. The electron emitter assembly of claim 13, wherein the mirror can rotate about at least two axes to reflect the light over a predetermined region to sequentially or randomly induce the plurality of photo-responsive devices to emit electrons.

15. The electron emitter assembly of claim 9, wherein each photo-responsive device comprises one of a photodiode and a phototransistor.

16. The electron emitter assembly of claim 9, wherein the light source comprises a laser.

17. An electron emitter assembly, comprising:
a first light source configured to emit light having a first wavelength;
a second light source configured to emit light having a second wavelength;
first and second photo-responsive devices operably coupled to an electron emitter device, the electron emitter device including a first electron emitter subassembly and a second electron emitter subassembly, the first photo-responsive device inducing the first electron emitter subassembly to emit electrons in response to receiving the light having the first wavelength, the second photo-responsive device inducing the second electron emitter subassembly to emit electrons in response to receiving the light having the second wavelength; and
an anode receiving the emitted electrons from the electron emitter device, the anode is configured to emit x-rays in response to receiving the emitted electrons from the electron emitter device.

18. The electron emitter assembly of claim 17, further comprising:
a housing having a light receiving window configured to allow light from the light source to pass therethrough, the photo-responsive device and the anode being disposed in the housing wherein the photo-responsive device is positioned to receive the light from the light source, the housing further comprising an x-ray transmissive window being disposed in an aperture extending through a wall of the housing, wherein the anode emits x-rays through the x-ray transmissive window in response to receiving the emitted electrons from the electron emitter device.

19. The electron emitter assembly of claim 17, wherein the electron emitter device comprises a field emitter array.

20. The electron emitter assembly of claim 17, wherein each photo-responsive device comprises one of a photodiode and a phototransistor.

21. The electron emitter assembly of claim 17, wherein the light source comprises a laser.

22. A method for generating an electron beam utilizing an electron emitter assembly, the electron emitter assembly having a housing with a light receiving window configured to allow light from a light source to pass therethrough, the electron emitter assembly further having a photo-responsive device, an electron emitter device, and an anode disposed in the housing, the method comprising:
emitting light from the light source that passes through the light receiving window of the electron emitter assembly onto the photo-responsive device operably coupled to the electron emitter device;
applying a voltage from the photo-responsive device to the electron emitter device in response to the photo-response device receiving the light to induce the electron emitter device to emit electrons towards the anode.

23. The method of claim 22, further comprising receiving the emitted electrons at the anode and generating x-rays at the anode in response to receiving the emitted electrons.

24. The method of claim 22, wherein the light comprises a laser light.

25. The method of claim 22, wherein the electron emitter device comprises a field emitter array.

26. A method for generating electron beams, comprising:
emitting light having a first wavelength onto a first photo-responsive device operably coupled to an electron emitter device, the electron emitter device having a first electron emitter subassembly and a second electron emitter subassembly;

energizing the first electron emitter subassembly to emit electrons towards an anode in response to the first photo-responsive device receiving the light having the first wavelength;

emitting light having a second wavelength onto a second photo-responsive device operably coupled to the electron emitter device;

energizing the second electron emitter subassembly to emit electrons towards the anode in response to the second photo-responsive device receiving the light having the second wavelength;

receiving the emitted electrons from the first electron emitter subassembly at the anode and emitting x-rays from the anode in response to the anode receiving the emitted electrons from the first electron emitter subassembly; and receiving the emitted electrons from the second electron emitter subassembly at the anode and emitting x-rays from the anode in response to the anode receiving the emitted electrons from the second electron emitter subassembly.

27. The method of claim 26, wherein each photo-responsive device comprises one of a photodiode and a phototransistor.

* * * * *